United States Patent
Skelding

(10) Patent No.: US 10,782,168 B2
(45) Date of Patent: Sep. 22, 2020

(54) APPARATUS AND METHOD FOR FLARE FLOW MEASUREMENT

(71) Applicant: Able Instruments & Controls Ltd, Reading (GB)

(72) Inventor: Anthony P. Skelding, Swindon (GB)

(73) Assignee: Able Instruments & Controls Ltd, Reading (GB)

( * ) Notice: Subject to any disclaimer, the term of this patent is extended or adjusted under 35 U.S.C. 154(b) by 289 days.

(21) Appl. No.: 15/866,321

(22) Filed: Jan. 9, 2018

(65) Prior Publication Data
US 2018/0195889 A1  Jul. 12, 2018

(30) Foreign Application Priority Data

Jan. 10, 2017 (GB) .................................. 1700428.4
Oct. 31, 2017 (GB) .................................. 1717928.4

(51) Int. Cl.
*G01F 1/66* (2006.01)
*G01F 1/34* (2006.01)
(Continued)

(52) U.S. Cl.
CPC ................ *G01F 1/667* (2013.01); *G01F 1/34* (2013.01); *G01F 1/66* (2013.01); *G01F 1/662* (2013.01);
(Continued)

(58) Field of Classification Search
CPC combination set(s) only.
See application file for complete search history.

(56) References Cited

U.S. PATENT DOCUMENTS

| 4,754,650 A | 7/1988 | Smalling et al. |
| 4,914,959 A | 4/1990 | Mylvaganam et al. |

(Continued)

FOREIGN PATENT DOCUMENTS

| DE | 10 2012 109 234 A1 | 4/2014 | |
| EP | 2 074 432 B1 | 4/2011 | |
| WO | WO-2008033035 A1 * | 3/2008 | ............. G01F 1/667 |

OTHER PUBLICATIONS

Svilainis, L., et al., "Excitation Signal's Influence on Ultrasonic Transit Time Flow Meter's Performance," *IOP Conf. Series: Materials Science and Engineering*, 42:1-4 (2012).

(Continued)

*Primary Examiner* — Jennifer E Simmons
(74) *Attorney, Agent, or Firm* — Morse, Barnes-Brown & Pendleton, P.C.; Sean D. Detweiler, Esq.

(57) ABSTRACT

Gas flow metering apparatus for obtaining flow measurements in respect of gas in a conduit is provided. The apparatus includes an ultrasonic mass flow meter including a first, upstream ultrasonic transducer, a second, downstream transducer, and a first calculation module for receiving data representative of an ultrasonic transit time between said transducers and calculating, using said data, a first flow velocity of said gas. The apparatus including at least one measurement device for measuring a flow parameter of said flow of gas through said conduit, a second calculation module for calculating, using said flow parameter, a second flow velocity of said gas, a verification module configured to select a preferred flow velocity from said first and second calculated flow velocities dependent upon expected accuracy in current gas flow conditions, and an output module for calculating, using said selected preferred flow velocity, a volumetric flow in respect of said gas flow.

20 Claims, 12 Drawing Sheets

(51) Int. Cl.
*G01F 1/68* (2006.01)
*G01N 29/024* (2006.01)
*G01F 7/00* (2006.01)
*G01N 29/22* (2006.01)
*G01F 25/00* (2006.01)
*G01N 9/24* (2006.01)
*G01N 29/036* (2006.01)
*G01N 33/00* (2006.01)

(52) U.S. Cl.
CPC ............... *G01F 1/68* (2013.01); *G01F 7/00* (2013.01); *G01N 29/024* (2013.01); *G01N 29/222* (2013.01); *G01F 25/0007* (2013.01); *G01N 9/24* (2013.01); *G01N 29/036* (2013.01); *G01N 33/0036* (2013.01); *G01N 2291/017* (2013.01); *G01N 2291/02836* (2013.01)

(56) References Cited

U.S. PATENT DOCUMENTS

| | | | |
|---|---|---|---|
| 6,286,360 B1* | 9/2001 | Drzewiecki | A61B 5/083 702/24 |
| 8,965,713 B2 | 2/2015 | Skelding | |
| 2002/0124660 A1* | 9/2002 | Drzewiecki | F15C 1/22 73/861.19 |
| 2005/0125170 A1* | 6/2005 | Gysling | G01F 1/666 702/48 |
| 2007/0151333 A1* | 7/2007 | Paradise | F01D 17/08 73/114.35 |
| 2008/0223129 A1* | 9/2008 | Gysling | G01F 1/74 73/32 A |
| 2011/0153225 A1 | 6/2011 | Mangal et al. | |
| 2012/0055263 A1 | 3/2012 | Konzelmann | |
| 2012/0173169 A1 | 7/2012 | Skelding | |
| 2014/0303909 A1* | 10/2014 | Hanks | G01F 1/68 702/47 |
| 2015/0086888 A1* | 3/2015 | Tsukagoshi | G01F 1/66 429/425 |
| 2016/0146653 A1 | 5/2016 | Skelding | |

OTHER PUBLICATIONS

European Search Report, European Application No. EP 18 15 0757, dated Jun. 8, 2018.

* cited by examiner

APPARATUS AND METHOD FOR FLARE FLOW MEASUREMENT

RELATED APPLICATIONS

This application claims priority to, and the benefit of, United Kingdom Application GB1700428.4, filed Jan. 10, 2017 and United Kingdom Application No. GB1717928.4, filed Oct. 31, 2017. The entire teachings of the above application(s) are incorporated herein by reference.

FIELD OF THE INVENTION

This invention relates generally to a method and apparatus for flare flow measurement.

BACKGROUND

A gas flare, or flare stack, is a gas combustion device used in industrial plants such as petroleum refineries, chemical plants, natural gas processing plants, as well as at oil or gas production sites having oil wells, gas wells, offshore oil and gas rigs, and landfills. Gas flaring at many oil and gas production sites protects against the dangers of over-pressuring industrial plant equipment. For example, when petroleum crude oil is extracted and produced from onshore and offshore oil wells, raw natural gas associated with the oil is brought to the surface as well. Especially in areas of the world lacking pipelines and other gas transportation infrastructure, vast amounts of such associated gas are commonly flared as waste or unusable gas. The flaring of associated gas may occur at the top of a vertical flare stack, or it may occur in a ground-level flare in an earthen pit. When industrial plant equipment items are over-pressurised, the pressure relief valve is an essential safety device, usually required by industrial design codes, standards and law, that automatically releases gases. The released gases are routed through large piping systems to a vertical elevated flare and burned as they exit the flare stacks. The size and brightness of the resulting flame depends on the flare gas flow rate.

As state, national and international government regulations for monitoring flare gas emissions become stricter, so do the demands for measuring and recording them. Environmental authorities around the world are requiring process plant operators to continuously monitor and record flare emissions and associated flow rates and gas composition. As a result of these new regulations, the industry has adapted by developing various methods to reduce emissions, which in turn has brought the need for higher accuracy measurement at lower flow rates.

Flare gas flow measurement is a challenging application, and with emerging regulations it has become even more challenging. Historically, flow meter technologies, including differential-pressure, vortex-shredding, and insertion thermal mass meters, have been somewhat limited in these applications because of their limited turndown, inability to follow unsteady flows, corrosion, intolerance of liquid carryover and sensitivity to changes in gas composition. Ultrasonic technology was developed for flare gas measurement some years ago and, today, ultrasonic flow meters are the industry standard for flare gas measurement.

One of the largest advantages of ultrasonic technology is its large turndown ratio; in other words, its ability to operate at atmospheric pressure with a high degree of accuracy over a large velocity range (better than 2.5 to 5% from 0.05 to 120 m/s). Referring to FIG. 1 of the drawings, the flow measurement is derived from the ultrasonic transit time between two transducers 100a, 100b which are mounted, within openings in the peripheral wall of the gas pipe 102, at an angle of 45° to the flow (depicted by arrow 104). Although the transducers 100a, 100b are effectively in contact with the gas in that they are inserted through the pipe wall, they are considered "non-invasive" because they are not inserted far enough into the actual flow path to impede the gas flow. As is typical with ultrasonic (flow) meter (USM) technologies, the primary measurement is flow velocity. The volumetric flow is then calculated based upon the area of the pipe. The meter uses pressure and temperature transmitters to calculate the standardised flow, where the volume measurement is adjusted to show what the measurement would be at standardised conditions. For flare gas applications, these are usually 15° C. at 1.01325 BarA. The pressure and temperature transmitters are also used to calculate a mass flow measurement, where the density is derived from the sound velocity of the gas measured from the ultrasonic signal transmission timing.

FIG. 2 illustrates a typical installation set-up with the pressure and temperature measuring points. The transducers 100a, 100b are typically inserted into the line through ball valves to enable extraction and closing off of the line during removal. The pressure transmitter 106 and the density transmitter 108 are also illustrated. This technology is well proven and has, in general, superseded previous methods since it meets the newest accuracy requirements dictated by flare emission legislative bodies.

However, there are some unavoidable limitations associated with this technology. For example, due to the physical location and installation method of these meters, it is very difficult to independently verify their performance. For this reason, some are built into spools and the spools can be tested and calibrated at a certified facility. This has also been used to give an indication of confidence, since the "out of the box" performance can be measured. In general, this does help to improve the reliability of the intrinsic flow calculation of the meters. However, due to the ever increasing importance of environmental pollution targets and associated taxation of $CO_2$ emissions, even more accurate means for verification of the measurement are continuously sought within the industry.

Furthermore, there has been increasing awareness of the limitations of the measurement when it is most needed, namely at the exceptionally high velocity flow rates that occur during emergency flaring conditions known as "blowdown", when all produced gas must be instantaneously sent to the flare. It is not unknown during "blowdown", in at least some industrial sites, for the flare gas velocity to exceed 800 m/s, which is close to 2.5 times the speed of sound (Mach 2.5) and twice the speed of a bullet. As effective as the above-described ultrasonic technology is, its upper limit of 120 m/s means it is completely incapable of providing a measurement at these "blowdown" velocities.

Still further, another limiting factor for all ultrasonic flare meters is gas stratification. Some flare gas compositions include gases of very different densities. Indeed, some common gases have twice the density of the lighter flare gases. For example, Methane has a density of 0.688 $kg/m^3$ whilst nitrogen has nearly twice the density at 1.165 $kg/m^3$, with ethane having virtually twice the density of methane and propane having nearly 2.5 times the density of methane. A so-called 'chirp' signal is typically transmitted between the ultrasonic transducers 100a, 100b in order to perform the required flow measurement. A chirp signal is a signal in which the frequency increases or decreases with time. At near to static and very low velocity flows, flare gas containing mixtures of different densities will separate and stratify into different density layers and, referring to FIG. 3 of the drawings, speed of sound changes with density through stratified layers of different gases, generating turbulence in refractive distortions of the speed and frequency of the sound propagation through the stratification layers of these gas mixtures. This is especially notable with large density changes, such as between methane and nitrogen. Change in speed and frequency is reversed when transmitted in the opposite direction, and the integrity of the chirp signal is thus corrupted when the ultrasound signals pass through a mixture of gases whenever the gas has separated into unstable and/or layered mixtures. The different absorption properties of the various gases can lead to some ultrasonic absorption of the chirp signal, especially at the lower frequencies, but the presence of any significantly different density gas component, especially with ultrasonic absorption properties, does not just affect the signal in the absorption band: the sweeping effect of the chirp signal replicates the same refractional wave behaviour as experienced when propagated through layers of gases (FIG. 3) therefore a refractional distortion is created as the chirp signal sweeps through the absorption band, and the distortion is directional, i.e. upstream to downstream distortion will be opposite to the downstream to upstream refractional distortion. This results in impairment of all conventional signal processing, and contributes significantly to the potential inaccuracy of known USM flow rate measurement techniques. The above-described stratification is thought to affect all available ultrasonic flow meters, as they all use the speed of sound in the gas between the transducers as a fundamental part of the measurement principle, and stratified gas will distort the directional computation.

Aside from the impairment of the conventional signal processing, there are additional uncertainties that are introduced due to differences in gas composition such as changes in gas compressibility. Ultrasonic flare meters have been proven to be highly accurate over the wide velocity range which is typically between 0.05 and 110 metres per second, with tests against traceable standards proving low uncertainties that meet the fiscal requirements in air and nitrogen calibration facilities where the gas compressibility is effectively a factor of 1. However, the typical flare gas composition is a complex mixture of assorted flammable and inert gases resulting in a very different compressibility to air or nitrogen.

The inventor(s) have a long working experience with flare metering and ultrasonic flow metering, and have noted that whilst the results are always very good on air and nitrogen calibration loops, on the rare occasions that testing has been performed on natural gas facilities the results have greater uncertainty, especially for the mass flow measurement. The inventor(s) have concluded that the principle difference between test flow runs using air and nitrogen compared to natural gas mixtures is that they compress differently to air and nitrogen at different pressures and temperatures. This in turn introduces further uncertainty in the flare measurement. The inventor(s) have noted that this effect manifests itself as a recognizable distortion in the test results data.

In the majority of the flare meters the gas mixture for a particular platform or refinery installation is measured and known, and the subject of regular laboratory analysis. However, the compressibility in the flare meter is nearly always left at a default of 1 since the capability to either dynamically or regularly calculate or enter the compressibility into the flare meter for the specific gas mixture has not been provided for in the flare metering system or equipment regardless of the flare technology employed. In nearly all cases the gas compressibility of natural gas is less than 1, and the overall effect of not adjusting for the compressibility of the natural gas is over reporting of the emissions greenhouse gases. Whereas to correctly report the amount of emissions by using the gas compressibility correction would reduce the entire calculation of all greenhouse gas emissions from flare stacks.

Yet another limitation of USM is the loss of measurement due to probe contamination, of which there is a higher risk during blowdown and high velocity flaring.

There are known gas flow technologies which have been used to measure flare velocities. An example of this type of technology is a thermal mass flow meter that uses probes inserted into the flow. However, a big limitation of a thermal dispersion probe is that it is only a single point measurement and not fully representative of the flow profile of the whole pipe. Also at such extremely high flow velocities, the gas flow generates violent wake frequencies that destroy inserted probes because the sudden outrush of gas also thrusts collected fragments of solids from the system up the flare stack which impact the probes and damage them. Yet if the probe is not inserted sufficiently into the flow it can only measure the flow velocity at the side wall resulting in greater uncertainty.

SUMMARY

It is an object of aspects of the present invention to address at least some of these issues and, in accordance with a first aspect of the present invention, there is provided Flare flow metering apparatus for obtaining flow measurements in respect of flare gas in a flare line, the apparatus comprising: an ultrasonic mass flow meter including:
- a first, upstream ultrasonic transducer and a second, downstream transducer, each transducer being mounted in a peripheral wall of a conduit, at an angle to the flow of flare gas therethrough; and
- a first calculation module for receiving data representative of an ultrasonic transit time between said transducers and calculating, using said data, a first flow velocity of said gas;
- at least one measurement device for measuring a flow parameter of said flow of gas through said conduit;
- a second calculation module for calculating, using said flow parameter, a second flow velocity of said gas;
- a verification module configured to select a preferred flow velocity from said first and second calculated flow velocities dependent upon expected accuracy in current gas flow conditions; and
- an output module for calculating, using said selected preferred flow velocity, a volumetric flow in respect of said gas flow.

The gas may optionally be flare gas and the conduit may optionally be a flare line.

In one exemplary embodiment of the present invention, each transducer may comprise a nozzle and wherein a pipe extends between the upstream transducer nozzle and the downstream transducer nozzle.

Optionally, the selection module may be configured to compare said first and second flow velocities with historical flow velocity data and select the preferred flow velocity based on this comparison. The selection module may optionally be configured to compare said first and second flow velocities with a historical average flow dataset to perform the selection of said preferred flow velocity.

According to an exemplary embodiment of the invention, the selection module may be configured to use an intelligent voting logic technique to perform the selection of the preferred flow velocity.

Optionally, the verification module may be configured to compare the flow velocity data obtained from the first calculation module and the flow velocity data obtained from the second calculation module, determine if there is a discrepancy therebetween, select one of the flow velocity data based on this comparison, and adjust the other flow velocity data in accordance with the selected flow velocity data.

In one exemplary embodiment, the apparatus may comprise a calibration module configured to utilise the selected preferred flow velocity as a master input for cross-calibrating the first and second flow velocities.

Optionally, the flow parameter may comprise the pressure differential between at least one of said transducers and said conduit. The flow parameter may optionally comprise the pressure differential between at least one of the transducers and the conduit.

According to an exemplary embodiment of the invention, the apparatus may comprise a second measurement device for measuring a second flow parameter of the flow of gas through the conduit; and a third calculation module for calculating, using the flow parameter, a third flow velocity of said gas, wherein the verification module is configured to select a preferred flow velocity from the first, second and third calculated flow velocities dependent upon expected accuracy in current gas flow conditions.

The transducers may optionally be mounted at a 45° angle to the flow of gas through the conduit.

In an exemplary embodiment, the apparatus may comprise a plurality of devices for measuring, at a plurality of respective locations, a pressure differential between at least one of the transducers and the conduit, wherein the second calculation module is configured to calculate, using data representative of the pressure differential measured at each of the plurality of locations, an average pressure differential and calculate, using data representative of the average pressure differential, a flow velocity of said gas.

Optionally, a chirp signal may be transmitted between said transducers for use in said determination of said ultrasonic transit time.

In an exemplary embodiment of the present invention, an ultrasonic signal comprising a sequence of individual frequency packets may be transmitted between the transducers for use in the determination of the ultrasonic transit time.

The apparatus may optionally comprise a signal control module for controlling a signal transmitted between the transducers for use in the determination of said ultrasonic transit time. The signal control module may be configured to, alternately or selectively cause one of: (i) a chirp signal, and (ii) an ultrasonic signal comprising a sequence of individual frequency packets to be transmitted between the transducers.

According to one exemplary embodiment of the invention, the first calculation module may be configured to perform a spectral analysis of the composition of the gas and compute, using data obtained from the spectral analysis, the ultrasonic transit time, or additionally from infrared transmitter and receiver devices inserted in the transducer faces.

Optionally, the first calculation module may be configured to obtain, from the spectral analysis, data representative of a quantity of a specified gas within the gas flow.

In an exemplary embodiment, the specified gas may be nitrogen.

The first calculation module may optionally be configured to omit data representative of the specified gas in the calculation of the flow velocity.

In an another exemplary embodiment, the first calculation module may be configured to obtain the gas compressibility from the gas composition data derived from the spectral analysis using either the ultrasonic or infrared absorption of gases.

The first calculation module may be configured to adjust the mass flow calculation according to said compressibility factor derived from the spectral analysis in real time.

In another exemplary embodiment, the first calculation module may be configured to directly interface with an online gas chromatograph and perform the same mass flow calculation adjustment according to said compressibility factor derived from the gas chromatograph data in real time.

According to an exemplary embodiment the pressure transmitter may be provided in the pipe extending between the upstream and downstream transducers, and a flow parameter in the form of a pressure differential may be measured between the upstream transducer nozzle and/or the downstream transducer nozzle and the pressure transmitter.

The pressure differential may optionally be measured at a location between the upstream transducer nozzle and the downstream transducer nozzle.

In an exemplary embodiment the apparatus may further include a dedicated chamber within said pipe, and a densitometer device associated with the chamber for measuring the density of the gas flowing through the conduit.

The densitometer may optionally be a non-invasive densitometer and comprise an ultrasonic crystal or time-of-flight measuring device.

Optionally, at least one of the transducers may include one or more additional pipe or spool nozzles.

According to a second aspect of the present invention there is provided, a method of flare flow metering to obtain flow measurements in respect of flare gas in a flare line, comprising:

using an ultrasonic mass flow meter including a first, upstream ultrasonic transducer and a second, downstream transducer, each transducer being mounted in a peripheral wall of a conduit defining said flare line, at an angle to the flow of flare gas therethrough, to obtain data representative of an ultrasonic transit time between said transducers and calculating, using said data, a first flow velocity of said gas; using at least one measurement device to measure a flow parameter of said flow of gas through said conduit, calculating, using data representative of said flow parameter, a second flow velocity of said gas, selecting a preferred flow velocity from said first and second calculated flow velocities dependent upon expected accuracy in current gas flow conditions, and calculating, using said selected preferred flow velocity, a volumetric flow in respect of said gas flow.

According to a third aspect of the present invention there is provided a method of flow metering to obtain flow measurements in respect of a fluid in a conduit, comprising:

providing an ultrasonic mass flow meter including a first, upstream transducer and a second, downstream transducer mounted in a peripheral wall of said conduit at an angle to the flow of fluid therethrough;

transmitting from said first transducer to said second transducer an ultrasonic signal comprising a sequence of individual frequency packets;

analysing each of the frequency packets received at said second transducer to identify any absorption of said signal by said fluid; and using said frequency packets received at said second transducer to calculate a flow velocity of said fluid.

According to a forth aspect of the present invention there is an alternative method provided to perform a spectral analysis of the composition of the gas and compute, using data obtained from infrared transmitter and receiver devices inserted in the transducer faces.

In this aspect of the invention, the infrared transmission is independent from the ultrasonic transmission, and the infrared devices are mounted either side of the transducer.

The infrared signal transmitting from said first transducer to said second transducer an infrared signal comprising a bandwidth of infrared frequencies, where specific gas components absorb specific infrared frequencies.

BRIEF DESCRIPTION OF THE FIGURES

These and other aspects of the present invention will be apparent from the following specific description in which embodiments of the present invention are described, by way of examples only, and with reference to the accompanying drawings, in which:

FIG. 10B is a schematic diagram showing data representative of a digitised, computer generated ultrasonic signal for comparison with FIG. 10a.

DETAILED DESCRIPTION

Figure 4:
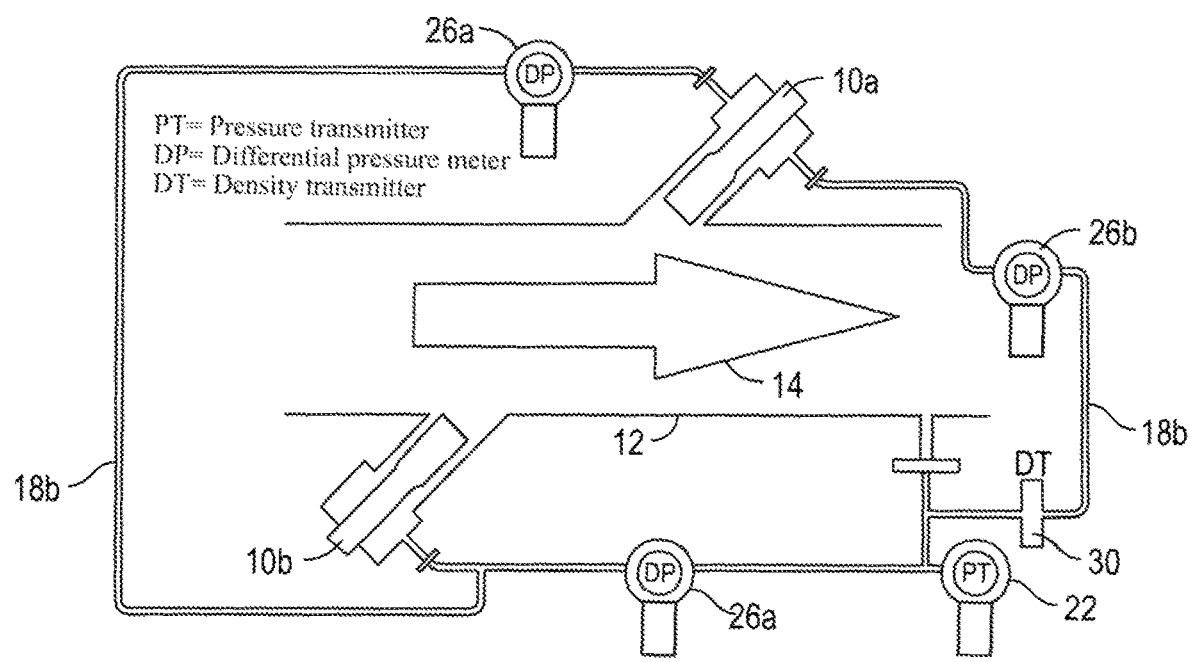
FIG. 4 is a schematic diagram illustrating apparatus according to an exemplary embodiment of the present invention for flare flow measurement.
Figure 5:
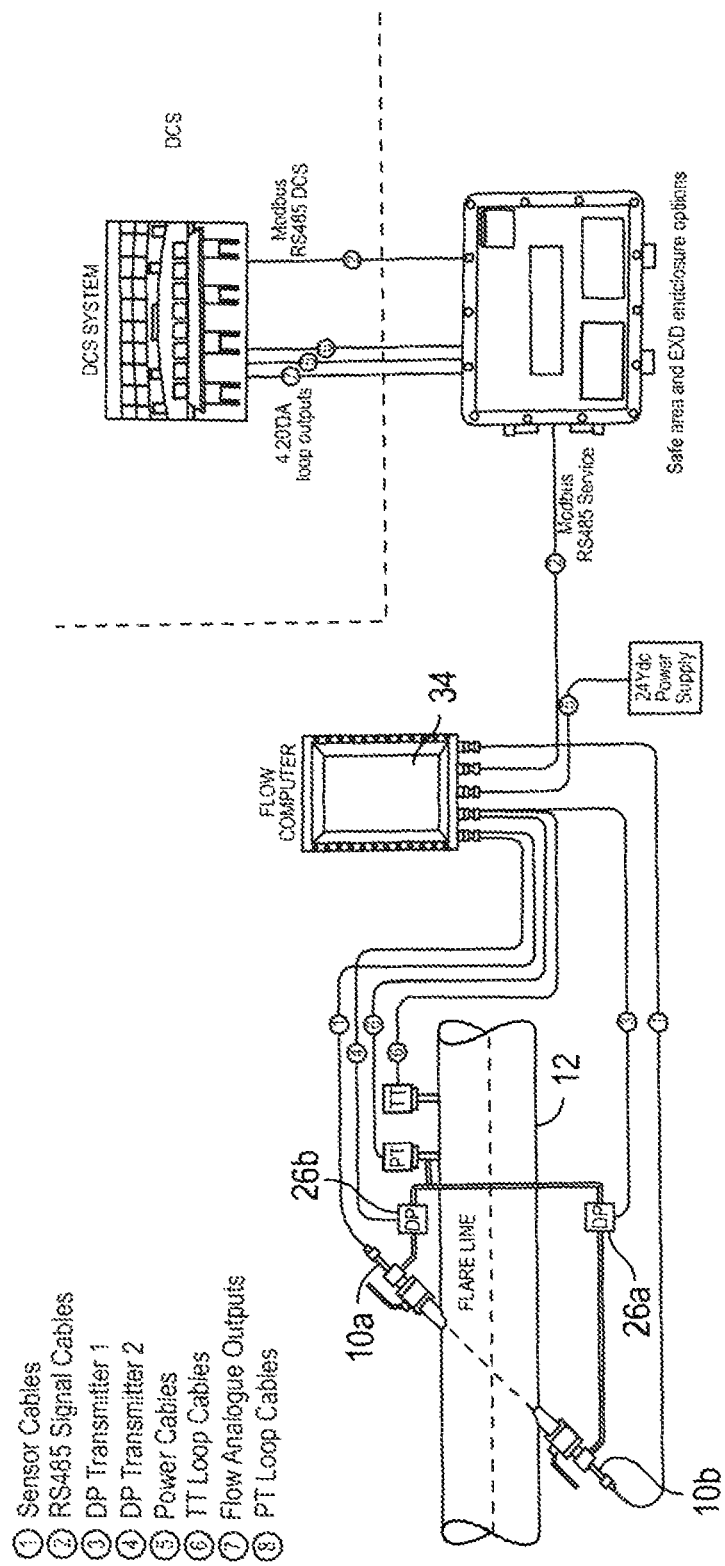
FIG. 5 is a schematic diagram illustrating an exemplary set-up configuration of the apparatus of FIG. 4.

Referring to FIG. 4 of the drawings, apparatus according to an exemplary embodiment of the present invention for flare flow measurement or metering comprises a conventional ultrasonic flare meter consisting of a pair of ultrasonic transducers 10a, 10b which are mounted, within openings in the peripheral wall of the gas pipe 12, at an angle of 45° to the flow (depicted by arrow 14). As before, and as will be known by a person skilled in the art, a flow measurement can thus be derived from the ultrasonic transit time between two transducers 10a, 10b. A typical flare stack installation includes a pipe network comprised of a first pipe section 18a, extending between the outlet of the upstream transducer 10b and the inlet of the downstream transducer 10a, and (at least) a second pipe section 18b extending from the outlet of the upstream transducer 10b to the outlet of the downstream transducer 10a. However, it will be appreciated by a person skilled in the art that the pipe network installation is dependent on the application and tends to be standardised for each size of flare stack pipe. The transducer nozzles tend always to be the same distance apart relative to the pipe schedule and, with few exceptions, the pressure and temperature probe nozzles (20—FIG. 5) tend always to be in exactly the same position relative to the measurement point. The pressure and temperature probe nozzles are installed in contact with the flow 14 by means of relative small bores in the peripheral wall of the pipe 12, the pressure probe nozzle will see a different pressure to that seen by the larger bore of the flare line (which is much larger). This pressure difference is directly proportional to the flow rate of the gas.

At zero flow, the pressure in the flare line and upstream transducer nozzle are virtually equal. However, at very high velocities, the difference in pressure is increased. This is because the vacuum draw on the limited small bore in the nozzle is further reduced by the transducer taking up most of the space, and this makes it read a substantially different pressure than the main pressure transducer 22 tapping point whenever there is significant flow. This difference is directly proportional to the flow rate, i.e. a "differential pressure" flow meter. This alternative pressure measurement point is facilitated by the fact that there is a conventional ultrasonic flow meter installation, such that the nozzles themselves provide alternative pressure measurement points. By measuring the differential pressures between the points, the derived velocity flow measurement can be calculated into a volume flow rate.

In the illustrated example, the differential pressure can be measured at three different meter points. At a first point 26a, the pressure difference between the upstream transducer holder and the main pipe pressure transmitter 22 can be measured. At a second point 26b, the pressure difference between the downstream transducer holder and the main pipe pressure transmitter 22 can be measured. At a third point 26c, the pressure difference between the upstream and downstream transducer holders can be measured. Once the flow has been calculated using one or more differential pressure measurements, the derived density measurement from the primary flare meter's gas sonic velocity measurement can be used to calculate a mass flow rate. Alternatively, a dedicated density measurement can be obtained using a dedicated chamber 30 in the main pressure transmitter line, using either a miniature USM Time of Flight principle or and external ultrasonic crystal method as detailed in, for example, GB2534452. It will be appreciated that, whilst a single pressure differential measurement can be used for these purposes, the combination of a number of pressure differential measuring points increases the accuracy of the resultant flow measurement, as described in more detail below.

By using the line pressure and temperature measurements, a standardised volumetric flow measurement may be derived from the mass flow measurement. The proposed system does not require any significant pipe work to install (and can, therefore, be retrofitted) by the addition of a few field components and a small processor, and since it is all based around small bore tubes, this installation may even be possible without shutdown of the flare stack. This has the additional advantage of removing the need to install the system using welding methods known in the art such as 'hot-tapping' which can be dangerous when working with flammable fluids and increases the risk of fire and/or explosions. Furthermore, there is no invasive probe, so there will be no associated vibration wake frequency or blockage issues even at high velocities. A typical installation is illustrated schematically in FIG. 5 of the drawings.

Figure 6:
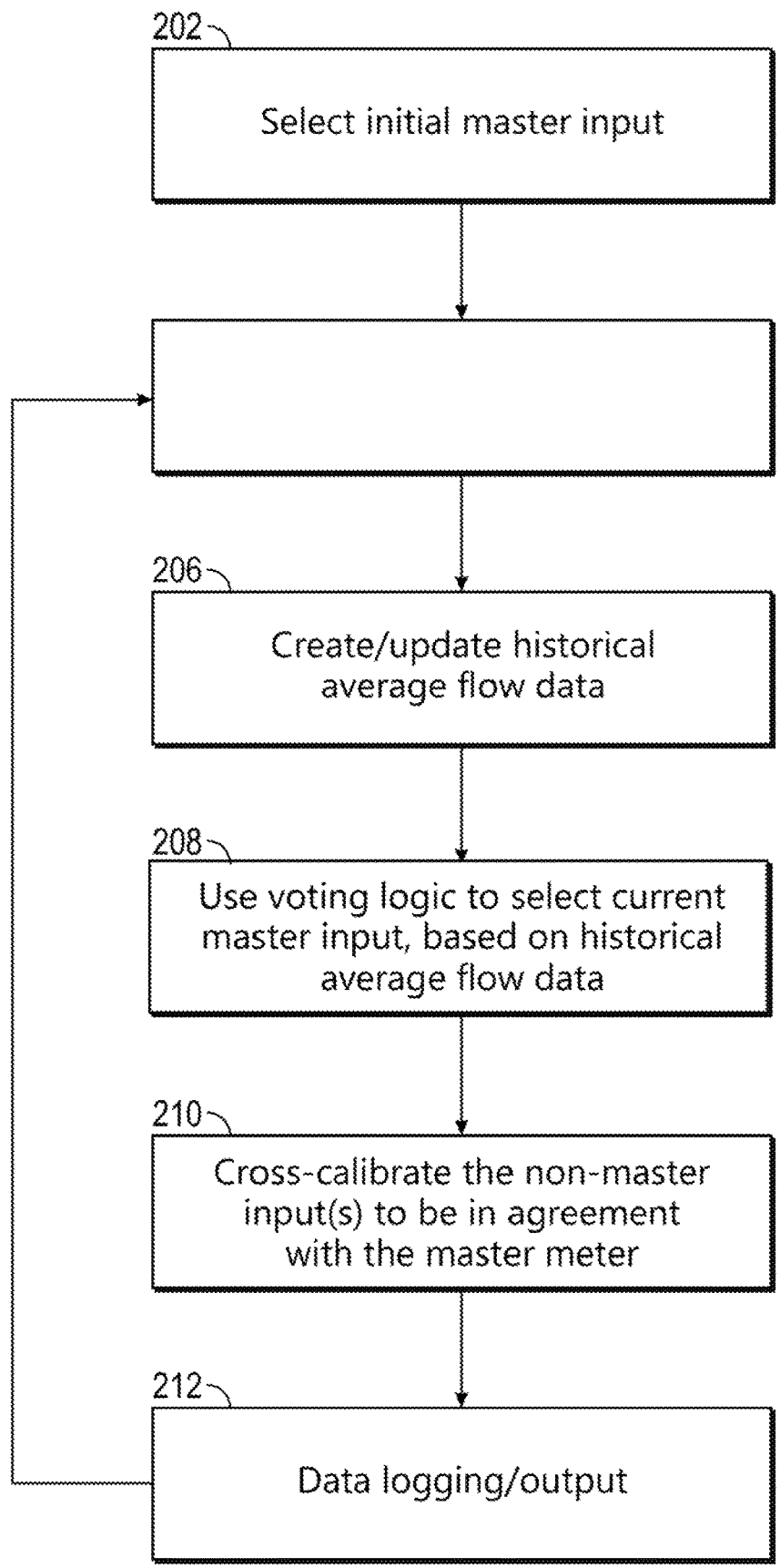
FIG. 6 is a schematic flow diagram illustrating a cross-calibration process for use in a method of flare flow measurement according to an exemplary embodiment of the present invention.

The differential pressure (DP) measurement method described above will typically have higher accuracy at higher flow rates where the pressure difference will be greater. However, at low flow rates, the DP measurement will be very small. Thus, the accuracy of the method can be improved by using multiple pressure sensing elements and taking an average. Then by using a cross calibration method, the differential pressure measurement can be cross calibrated to the USM flare measurement during the low flow ranges up to 120 metres per second velocity. Thus, referring to FIG. 6 of the drawings, in a cross calibration method that may be thus used, at step 202 the cross calibration module in the form of a computing device in the flow computer (34—FIG. 5) is initialised. At step 206 the computing device creates/updates a store of historical average flow data. The number of past measurement samples that are averaged, and the time period during which samples are collected, are variable parameters that can be selected during set-up of the apparatus, so as to adjust the sensitivity of the voting logic process. Measurement sample shift registers may be regularly updated so that older samples are overwritten as the new samples are taken.

At step 208, a voting logic technique is used to compare the incoming flow measurement calculated from a DP value (either a single value or an average of multiple values) to the historical data to determine which incoming measurement is considered to be the most reliable under the present changing process conditions in comparison with the historical trend. The incoming meter input having a historically stable measurement with low mean deviation that is nearest the historical average data is selected as the master input. The master flow measurement/input is expected to be the most accurate flow measurement during perfect conditions, and may be used to cross calibrate the flare line USM and the DP flow measurement mean values.

Flow rate data, thus collected, is output and/or logged at step 212.

Thus, the accuracy of the main (USM) meter can be independently verified during normal operation within a known degree of uncertainty and the secondary DP measurement also provides a means of dual redundancy by giving an alternative measurement during times of failure or maintenance of the main measurement equipment. During higher velocities, in excess of 120 m/s, the differential pressure method takes over when the primary USM meter no longer measures. This can be processed within a small PLC, with the PLC station effectively providing the complete solution, taking in both the primary and secondary measurements and giving one robust output supplying verification diagnostics. In other words, the redundant velocity measurement is not restricted by the limitations of the ultrasonic time of flight computation. It continues with its sonic velocity and gas density computation to ensure an accurate flow velocity measurement is achieved even when the velocity exceeds that which can be measured by ultrasonic means. At higher velocities, the secondary measurement becomes the primary, and its accuracy increases as the flow velocity increases, delivering unrivalled certainty even up to 1000 m/s.

Held within the PLC (included in the flow computer 34—FIG. 5), will be a nominal cross calibration curve, giving a constant second independent measurement that replicates and verifies the flow measurement at any flow rate. The curve can be obtained by recording differential pressure against the USM flare meter in normal operation, although such curves could alternatively be generated at an independent calibration facility. As previously stated, because the proposed flare meter installation is standardised for a given pipe size, the secondary (DP) method of flow measurement can have a standardised curve for each pipe size.

It will be understood by those skilled in the art that the secondary method of flow measurement does not necessarily need to be the differential pressure measurement method, and any suitable method as is known in the art may be used, for example thermal dispersion measurement or clamp on ultrasonic flow measurement may be used instead of or in addition to the differential pressure method.

Thermal dispersion is known in the art as a flow measurement principle however in prior art solutions it requires altering the pipeline or shutting the flare stack down in order to install retrospectively. An alternative exemplary embodiment of the present invention is provided, wherein the apparatus can be retrofitted (and therefore maintain the safety aspects associated with the retrofit method), as in the first exemplary embodiment of the present invention, but wherein the secondary measurement method comprises a thermal dispersive method.

Figure 9A:
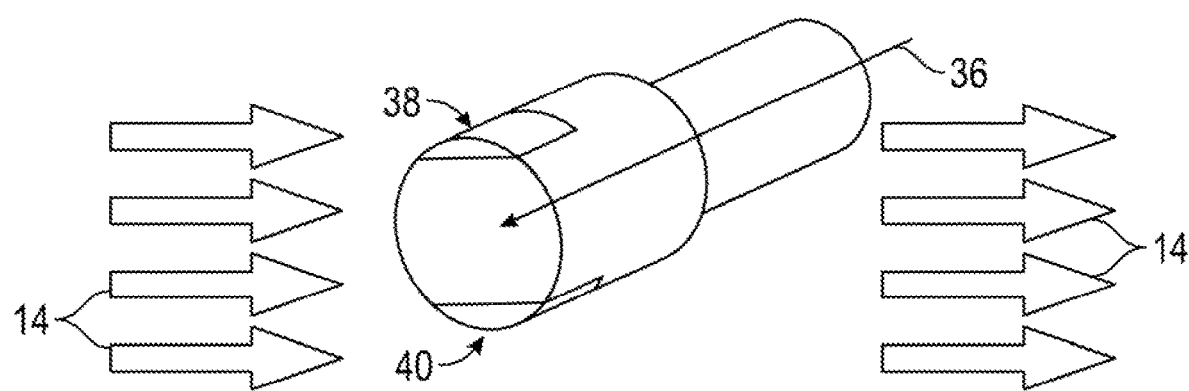
FIGS. 9A and 9B are schematic illustrations showing a further alternative method for measuring flow rate using thermal dispersive methods according to a further exemplary embodiment of the present invention.
Figure 9B:
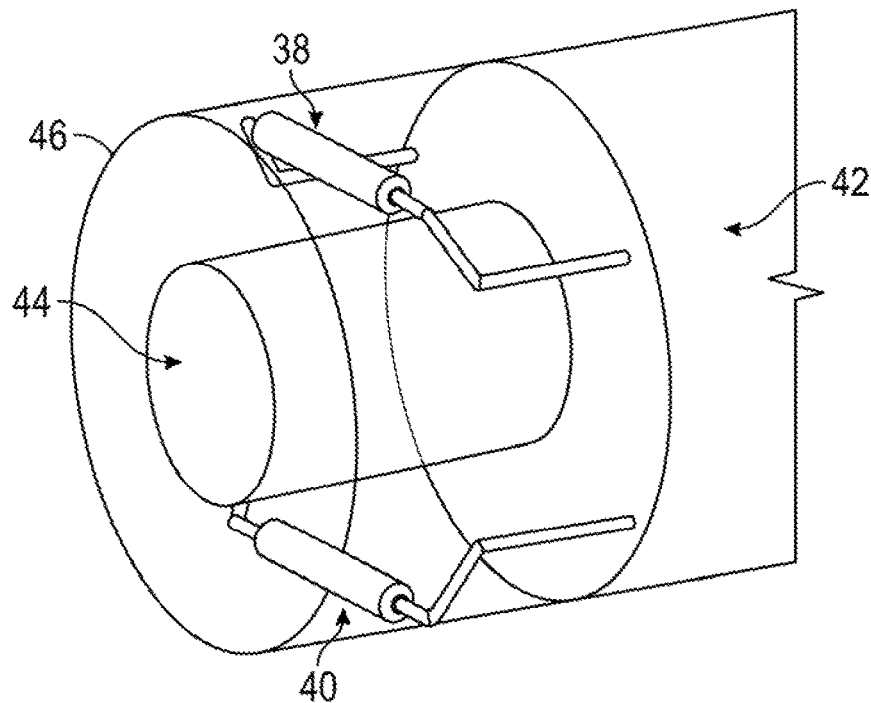

Referring additionally to FIGS. 9A and 9B of the drawings, ultrasonic transducers 10a, 10b are replaced with adapted ultrasonic transducers (not shown) which comprise a thermal dispersive element 36 at the distal end of each transducer. In order to increase the accuracy of the thermal dispersive method, the data is cross-calibrated as described above. This provides a further optional secondary method, which may be used additionally or alternatively to the transducer nozzle differential pressure measurement method.

The thermal dispersive elements 36 are in direct contact with the gas flow 14, and can have a heated sensor 38 fitted at least partially around the circumferential face of the cylinder, and a non-heated sensor 40 fitted at least partially around the circumferential face of the cylinder. The sensors measure the differential temperature of the gas flow. The gas flow computer can then calculate the flow velocity based on the fact that the temperature difference of the heated and non-heated sensor is directly proportional to the gas flow velocity. The mass flow velocity can then be calculated as described above.

In a further exemplary embodiment, the sensors may be provided directly on the end of the ultrasonic transducer, in what is known as a "potted assembly" 42. The heated and non-heated elements 38, 40 fit on an end of the transducer, angled away from the ultrasonic tip 44 of the transducer but contained within a cover 46.

Figure 10A:
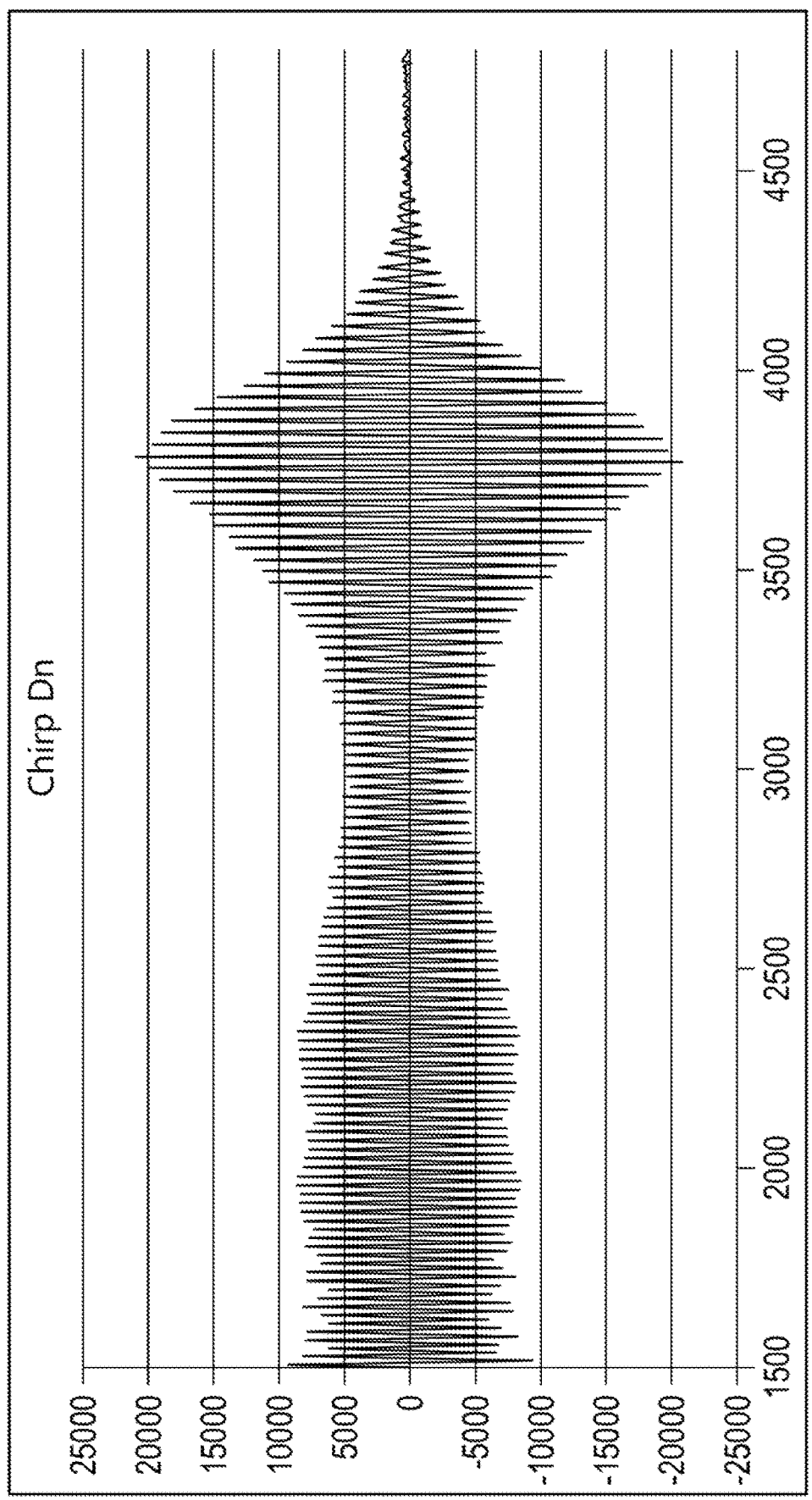
FIG. 10A is a schematic diagram showing data representative of an analogue ultrasonic signal measured using the apparatus according to one exemplary embodiment of the present invention.
Figure 10B:
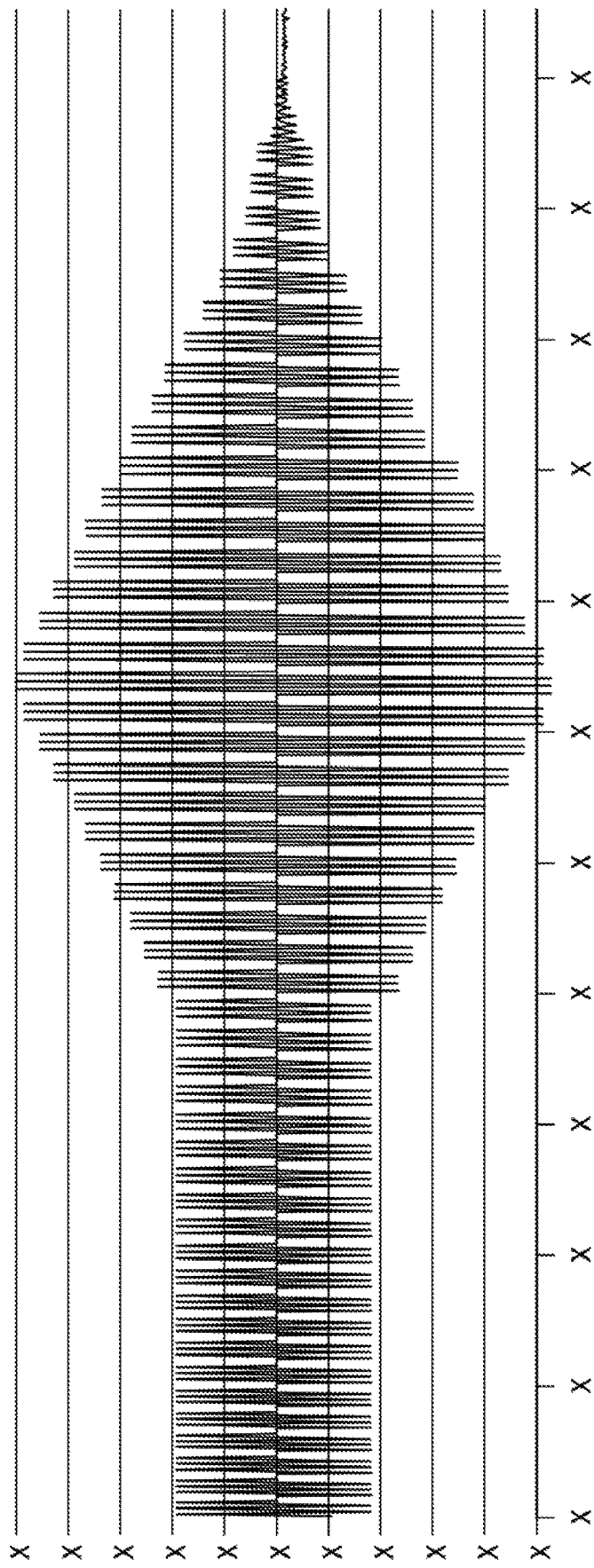
Figure 10C:
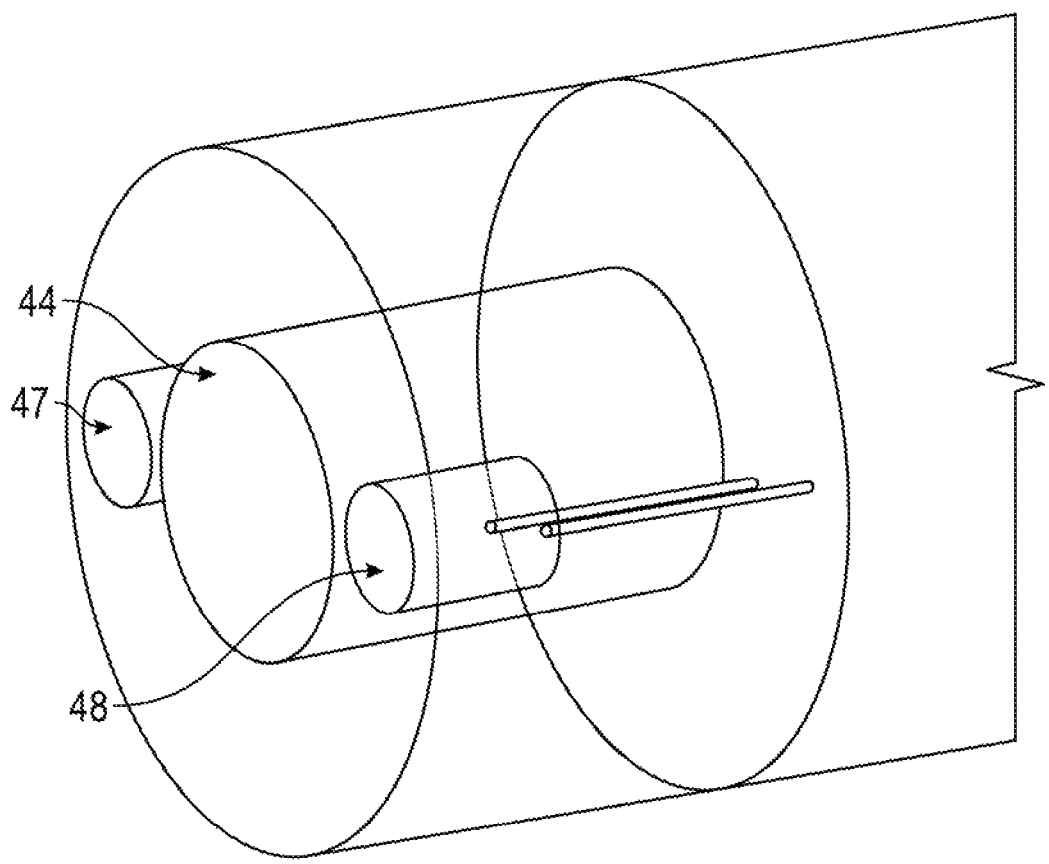
FIG. 10C is a schematic partial diagram illustrating apparatus according to an exemplary embodiment of the present invention.

Referring additionally to FIG. 10C, in a further exemplary embodiment optical infrared transmitter 47, and infrared receiver 48, optical may be provided in the "potted assembly" with their active faces on the face of the transducer assembly on either side of the ultrasonic crystal 44. The computer can perform a spectral gas analysis by the specific absorption of the certain infrared frequencies transmitted between the transducers. The gain of the transmission can be automatically adjusted to adjust for deposits on the face of the transducers.

It can be understood that if "hot tapping" is permissible, or there is a flare metering spool which can easily be adapted, then the invention can include any number of additional nozzles into the flare line to allow any type of alternative secondary measurement, including clamp-on ultrasonic technologies. The invention is able to perform voting logic and cross calibration across any number of available secondary measurements to achieve the optimum performance for the changing flare gas conditions.

Figure 1:
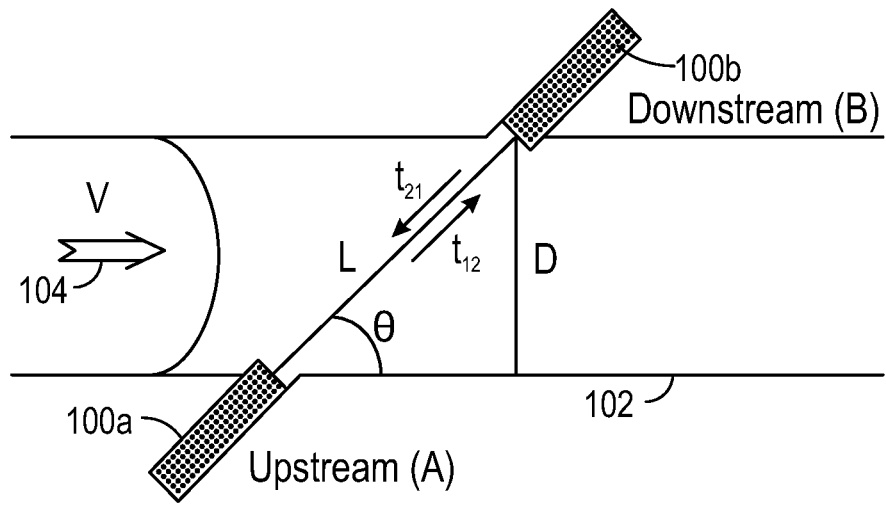
FIG. 1 is a schematic diagram illustrating an ultrasonic flare meter according to the prior art using the known transit time measurement principle.
Figure 2:
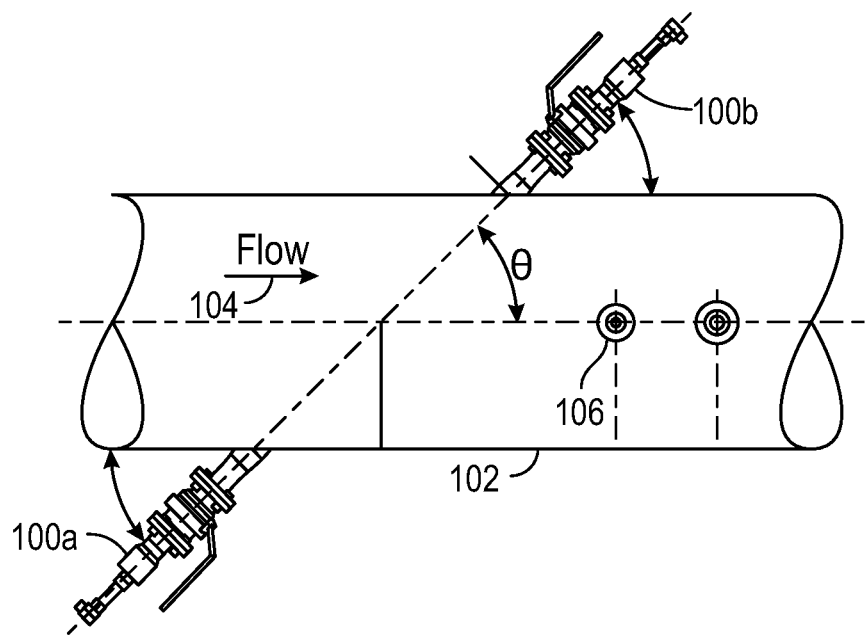
FIG. 2 is a schematic diagram illustrating an ultrasonic flare meter transducer installation according to the prior art with ball valves and pressure and temperature transmitter probes downstream of the measurement point.
Figure 3:
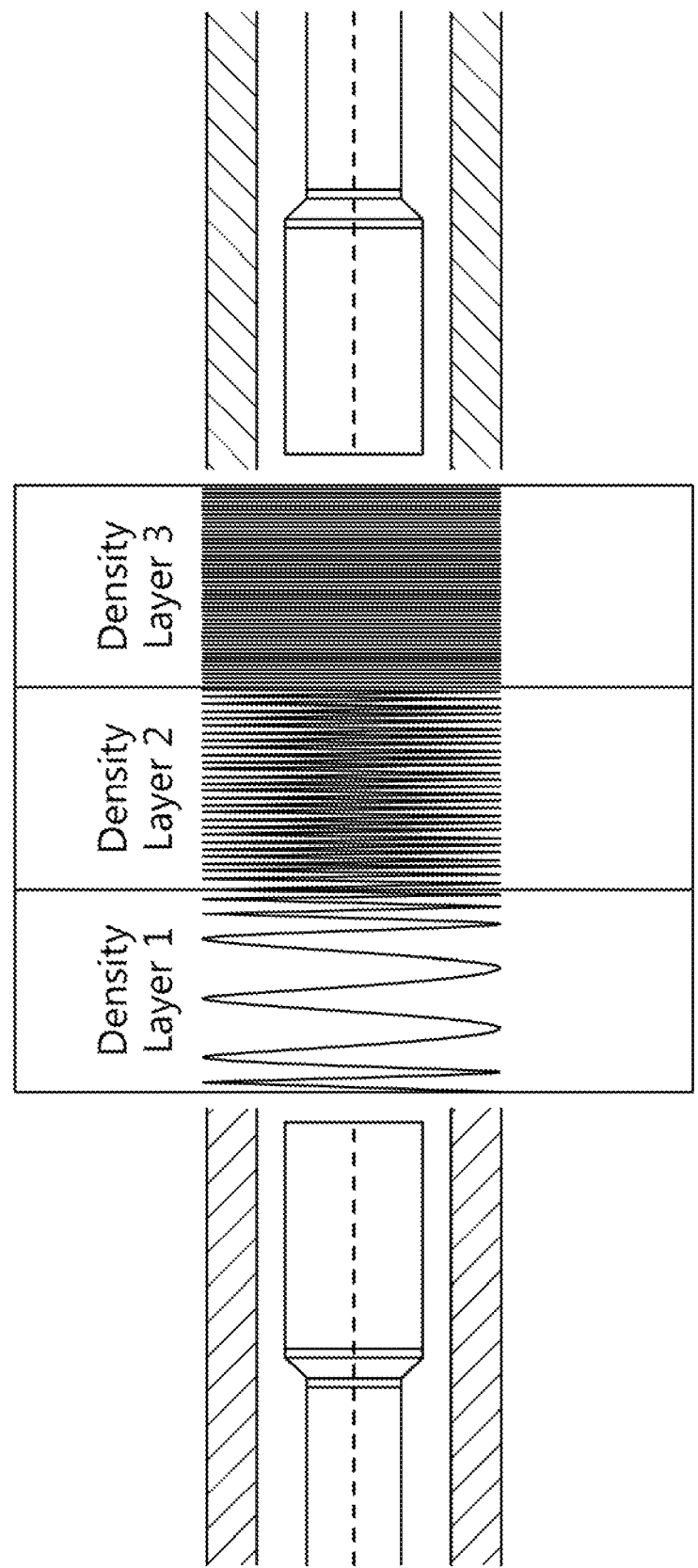
FIG. 3 is a schematic illustration of a chirp signal passing through three different gas layers, each having a different density.

As explained above, speed of sound changes with density through stratified layers of different gases, generating refractive distortions of the speed and frequency of the sound propagation through turbulence in the stratification layers of these gas mixtures. This is especially notable with large gas density disparities as between Methane and Nitrogen. Change in speed and frequency is reversed when transmitted in the opposite direction, and the integrity of the chirp signal used in conventional ultrasonic flow rate meters is thus corrupted when the ultrasound signals pass through a mixture of gases whenever the gas has separated into unstable and/or layered mixtures. The different absorption properties of the various gases can lead to some ultrasonic absorption of the chirp signal, especially at the lower frequencies, but the presence of any significantly different density gas component, especially with ultrasonic absorption properties, does not just affect the signal in the absorption band: the sweeping effect of the chirp signal replicates the same refractional wave behaviour as experienced when propagated through layers of gases (FIG. 3) therefore a refractional distortion is created as the chirp signal sweeps through the absorption band, and the distortion is directional, i.e. upstream to downstream distortion will be opposite to the downstream to upstream refractional distortion. This results in impairment of all conventional signal processing, and contributes significantly to the potential inaccuracy of known USM flow rate measurement techniques. The above-described stratification is thought to affect all available ultrasonic flow meters, as they all use the speed of sound in the gas between the transducers as a fundamental part of the measurement principle, and stratified gas will distort the directional computation.

Figure 7:
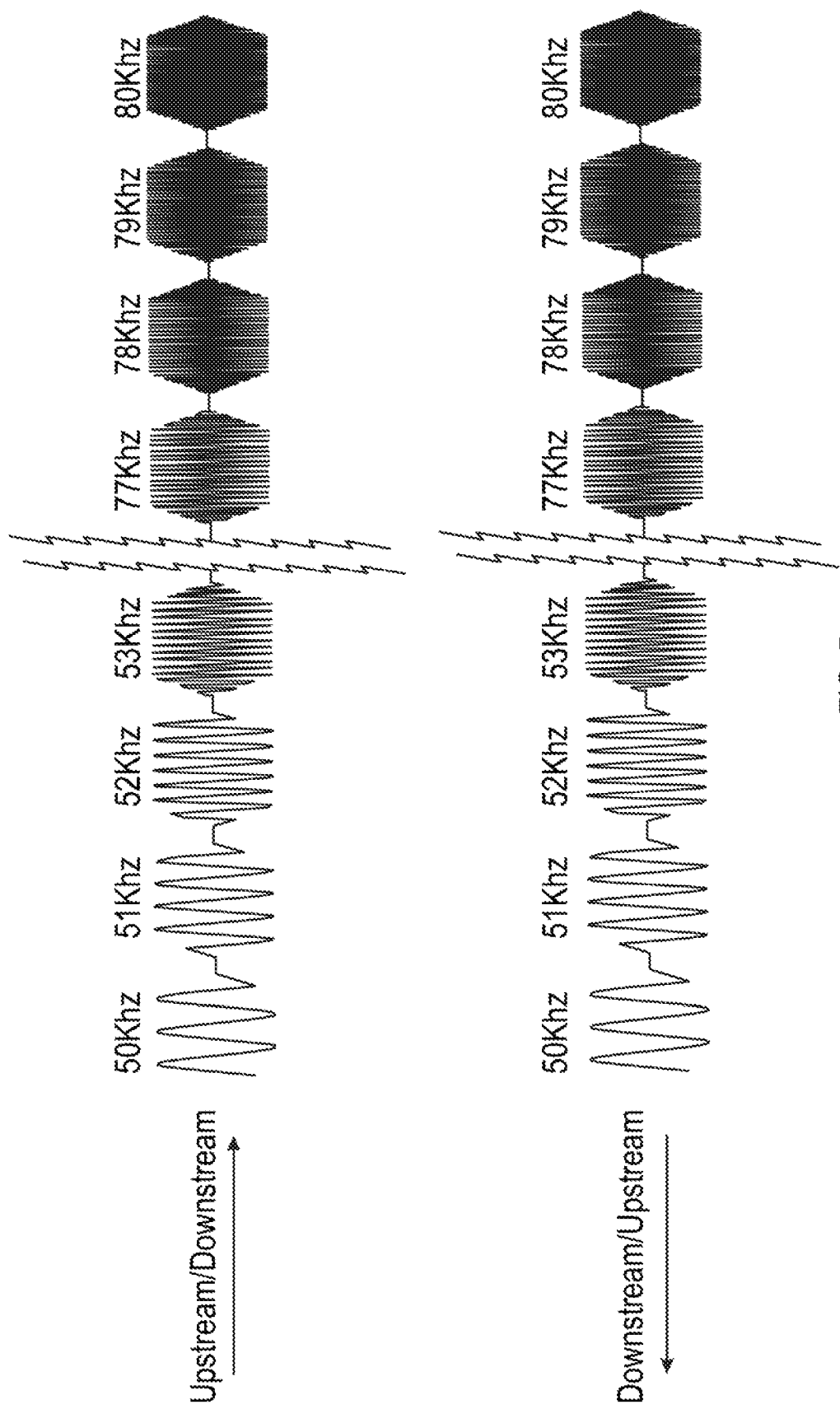
FIG. 7 is a schematic illustration of an alternative ultrasonic signal for use in an ultrasonic flow rate measuring device in apparatus according to an exemplary embodiment of the present invention.
Figure 8A:
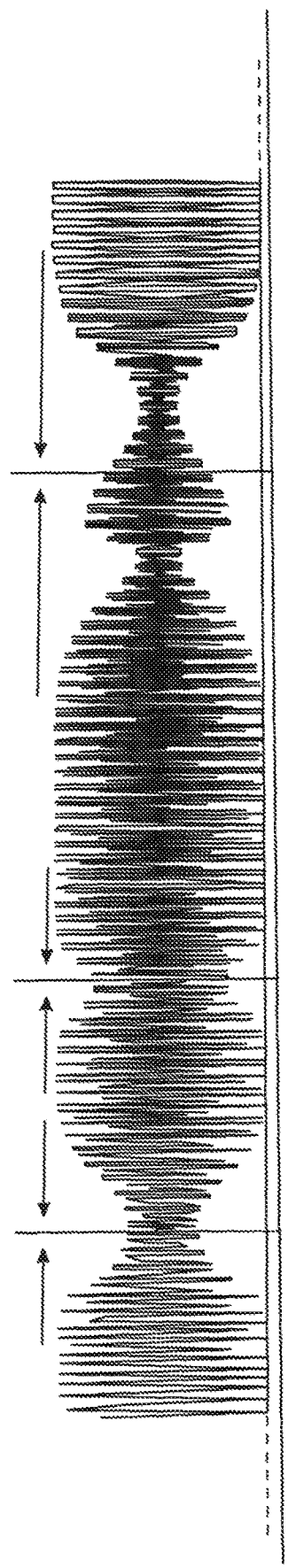
FIGS. 8A, 8B, 8C are schematic diagrams illustrating a further alternative ultrasonic signal for use in apparatus according to an exemplary embodiment of the present invention.

The inventors have therefore devised a new signal processing method to negate these gas refractional issues that are experienced when using varying sweep frequency signals by utilising a modular approach to the frequency spectrum. Rather than a continuous sweep of changing frequency, the invention instead uses individual single frequency packets (as illustrated in FIG. 7 of the drawings), which are transmitted between the transducers in sequence, in individual time slices, and the frequency of each single frequency packet is chosen according to a selected sequence, over time, under the control of a flow metering program. The signal processing program can select a sequence of any pattern of frequency packets. The signal processing program then can assemble these individual packets into a digitally generated equivalent sweep. The program can eliminate any unwanted frequency components by excluding them from the reassembled sweep envelope for the upstream and downstream transmissions. And overlay the envelopes for comparison by correlation. With the digitally generated and reconstructed chirp transmission, the effect of transmission losses experienced at high flow velocities in prior art solutions are significantly reduced, and this increases the maximum flow velocity which can be measured with the ultrasonic method. Referring to FIG. 8A, there is illustrated a section from the available ultrasonic spectrum transmitted in singular frequency time slice segments, showing areas of ultrasound absorption from absorbing gases. By using temperature and pressure the flow computer analyses the frequency and amplitude of these absorption frequency bands to calculate the gas composition by comparing the data to calibration test models. This allows the program to identify the present gasses within the flow pipe, and therefore calibrate the next ultrasonic transmission accordingly.

Figure 8B:
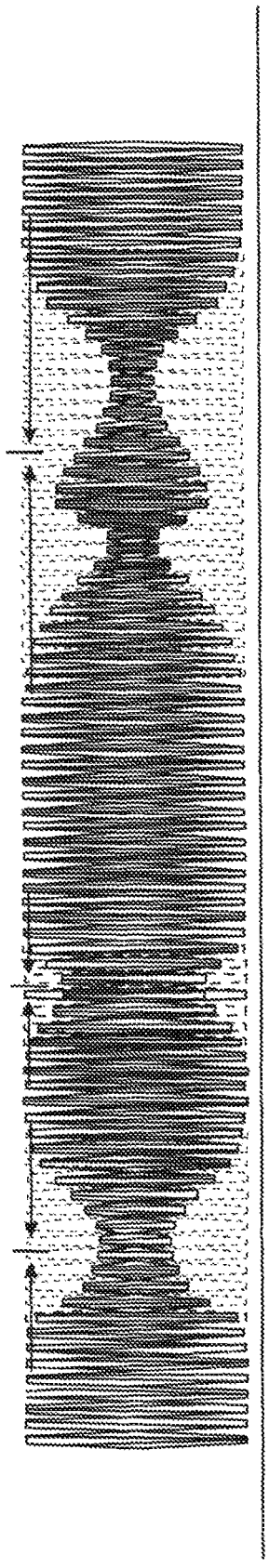

Referring to FIG. 8B of the drawings, in the present exemplary embodiment of the invention, for the next transmission the program avoids the frequencies affected by absorption and instead replaces them with repeats of the unaffected frequency time slices to complete a selective frequency chirp pattern. The known unaffected frequencies above and below the affected frequency band can be used to complete the chirp pattern. The processor can swap between gas composition transmissions where the chirp can measure gas composition, and then use selective frequency chirps for Time of Flight measurement. It would be understood by a person skilled in the art that these can be adjustable features in the setup program for certain flare gas applications.

Figure 8C:
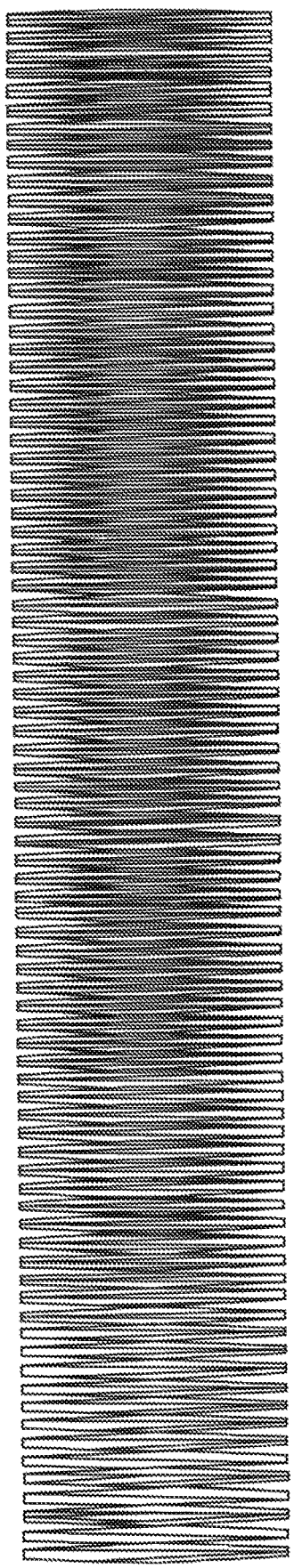

The resultant chirp is illustrated in FIG. 8C of the drawings. The upstream to downstream and downstream to upstream transmissions use this same selective frequency chirp pattern which ensures the timing measurement from the correlation of the chirp signals is achieved without being affected by the gases in the mixture that absorb certain frequencies. The selective chirp pattern of frequencies is dynamically chosen by the program in response to changes in pressure and temperature and gas composition to ensure the best chirp pattern is used for current conditions.

For the gas composition ultrasound spectroscopy transmission, the gain for the single frequency time slice segments can be adjusted automatically to ensure they have equal amplitude across the whole spectrum under normal conditions.

Conversely, for the Time Of Flight chirp transmission the amplitude of the single frequency segments need not be uniform, and may instead utilise the natural resonance of the ultrasonic crystals to produce a more efficient transmission. Yet it can also be understood that using the same method described, the amplitude of individual frequency time slices can also be adjusted through a setup or automatically by the processor in order to develop a perfect chirp signal shape in ideal conditions.

Further, it can be understood that this method of forming a selective frequency chirp from single frequency time slice segments permits the digital reprocessing of each individual segment. The resultant computation of the combined timing of all the single frequency segments in the selective frequency chirp enables a significantly improved timing comparison between the upstream and downstream transmissions, which significantly reduces the effect of transmission noise and distortion, ensuring correlation computations that are immune to the dynamics of analogue ultrasound transmission.

This method has even more immunity to noise than the conventional sweep signal processing. The correlation can also be extended, as the digitally generated sweep of frequencies sequence pattern can effectively be extended over any time frame. Referring specifically to FIG. 10A of the drawings, there is illustrated a real captured analogue chirp signal. This can be directly compared with a computer generated digitalised chirp signal as illustrated in FIG. 10B of the drawings. For the digitised signal the processor has full control over the waveform transmitted and received, and therefore it will be evident to those skilled in the art that digital reconstruction enables the timing information to be extracted even when the received signal has been significantly corrupted by any noise and transmission distortions. And the length and duration of the frequency segments can be automatically extended by the processor during periods of turbulence and erratic flow to reduce the uncertainty of the Time Of Flight measurement.

If there are gases in the in the flare mixture that absorb specific frequencies, or lead to refractive distortions at specific frequencies, then these frequencies can be removed from the sequence and replaced with any other frequency packet, which may also be a repeat of the previous frequency packet as described above. The frequencies may be chosen or rejected by the selection program based upon the analysis of the current measurement sequence, where analysis of the correlation of each frequency packet is continually monitored to assess its suitability for the current gas conditions.

As a direct consequence of the analysis of the integrity of the different frequencies in the spectrum of gases, it can be seen that the performance of the individual frequency packets is directly indicative of the presence of ultrasound absorbance of certain gases. By computation of this analysis against temperature and pressure the gas composition of the flare gas mixture can be ascertained.

It can therefore be understood that processing all the available frequencies in separate packets enables a spectrum analysis of the gas composition. Whereas computation of a sequence that ignores any packets that have any distorted effects permits a correlation of upstream to downstream and downstream to upstream timing that is immune to the effects of ultrasound absorption and refraction issues that are associated with the conventional frequency sweep technique used in Chirp signal processing.

It can be understood that gases that are irrelevant to the fiscal flare metering reporting requirement can therefore be quantified by this advanced method, facilitating their removal from the flare emissions calculation, i.e. Nitrogen.

It can be understood that this signal processing can be applied to any ultrasound Time Of Flight measurement, and the invention can be applied to work with liquid and gas flow measurements and to ultrasound analysis of solids. As well as enhancing the standard or conventional flow measurement through the above-described dual redundancy, and unlike other flare metering technology, there is a much higher upper velocity limit to the proposed measurement method. Indeed, it extends the overall velocity range toward 1000 m/s, thereby achieving velocity measurements in excess of Mach 3 without loss of reliable operation. There is currently no known metering method that comes close to this performance. In addition, an independent means of flow verification is provided, thereby providing a further improvement over the prior art.

The invention can be achieved without the use of inserted probes so that the apparatus is immune to wake frequencies and cannot be damaged by extremely high velocities that are often experienced during extreme blowdown conditions. If the DP lines become blocked or contaminated, they can be relatively easily maintained and restored by simply blowing the pipes clean. Aspects of the invention may provide an automatic or remote controlled means of checking the pipes for blockages and cleaning using, for example, nitrogen.

It will be understood by those skilled in the art, that the invention as described by way of exemplary embodiments above is not necessarily limited to flare gas metering and may be applied to any gas flow conduit. To summarise, aspects of the invention provide a flare gas flow metering method and apparatus which ensures that the flow measurement is reliable and repeatable under all process conditions regardless of extremes (both high and low) in flow velocities and significant diversity in gas densities. The maximum measurable flow velocity is also significantly increased compared with that achievable with other known arrangements. The embodiment described above offers dual redundant protection against loss of measurement under all process conditions, which is a common problem with known arrangements. The proposed arrangement is suitable for operation in high and low temperature applications, immune to the presence of both condensates and moisture, and compensates for any gas composition distortions to deliver a robust and reliable measurement method for both high and low velocity extremes, and uses a secondary redundancy measurement system to verify the timing of measurements through stratified gases, thereby enhancing the performance at low velocities and greatly improving the performance of flow computation.

It will be appreciated by a person skilled in the art, from the foregoing description, that modifications and variations can be made to the described embodiments without departing from the scope of the invention as defined by the appended claims.

What is claimed is:

1. Gas flow metering apparatus for obtaining flow measurements in respect of gas in a conduit, the apparatus comprising:
   an ultrasonic mass flow meter including:
   a first, upstream ultrasonic transducer and a second, downstream transducer, each transducer being mounted in a peripheral wall of said conduit, at an angle to the flow of gas therethrough; and
   a first calculation module for receiving data representative of an ultrasonic transit time between said transducers and calculating, using said data, a first flow velocity of said gas;
   at least one measurement device for measuring a flow parameter of said flow of gas through said conduit;
   a second calculation module for calculating, using said flow parameter, a second flow velocity of said gas;
   a verification module configured to select a preferred flow velocity from said first and second calculated flow velocities dependent upon expected accuracy in current gas flow conditions; and
   an output module for calculating, using said selected preferred flow velocity, a mass flow in respect of said gas flow.

2. Apparatus according to claim 1, wherein said gas is flare gas and said conduit is a flare line.

3. Apparatus according to claim 1, wherein said selection module is configured to compare said first and second flow velocities with a historical average flow dataset to perform the selection of said preferred flow velocity.

4. Apparatus according to claim 1, wherein said selection module is configured to use an intelligent voting logic technique to perform said selection of said preferred flow velocity.

5. Apparatus according to claim 1, wherein the verification module is configured to compare the flow velocity data obtained from the first calculation module and the flow velocity data obtained from the second calculation module, determine if there is a discrepancy therebetween, select one of said flow velocity data based on said comparison, and adjust the other flow velocity data in accordance with the selected flow velocity data.

6. Apparatus according to claim 1, comprising a calibration module configured to utilise said selected preferred flow velocity as a master input for cross-calibrating said first and second flow velocities.

7. Apparatus according to claim 1, wherein said flow parameter comprises the pressure differential between at least one of said transducers and said conduit, and/or a thermal dispersion measurement; and/or a clamp-on ultrasonic transducer measurement, wherein said pressure differential is measured at a location between said upstream transducer nozzle and said downstream transducer nozzle.

8. Apparatus according to claim 1, wherein at least one of said ultrasonic transducers includes thermal dispersion flow sensing elements and said flow parameter is a thermal dispersion measurement.

9. Apparatus according to claim 7, comprising a plurality of devices for measuring, at a plurality of respective locations, a pressure differential between at least one of said transducers and said conduit, wherein said second calculation module is configured to calculate, using data representative of the pressure differential measured at each of the plurality of locations, an average pressure differential and calculate, using data representative of said average pressure differential, a flow velocity of said gas.

10. Apparatus according to claim 1, comprising a second measurement device for measuring a second flow parameter of said flow of gas through said conduit; and a third calculation module for calculating, using said flow parameter, a third flow velocity of said gas, wherein said verification module is configured to select a preferred flow velocity from said first, second and third calculated flow velocities dependent upon expected accuracy in current gas flow conditions.

11. Apparatus according to claim 1, wherein a chirp signal is transmitted between said transducers for use in a determination of said ultrasonic transit time, or wherein an ultrasonic signal comprising a sequence of individual single frequency packets is transmitted between said transducers for use in a determination of said ultrasonic transit time.

12. Apparatus according to claim 11, wherein said first calculation module is configured to perform a spectral analysis of the composition of said gas and compute, using data obtained from said spectral analysis, said ultrasonic transit time, or wherein said first calculation module is configured to obtain, from said spectral analysis, data representative of a quantity of a specified gas within said gas flow.

13. Apparatus according to claim 12, wherein said first calculation module is configured to omit data representative of said specified gas in said calculation of said flow velocity.

14. Apparatus according to claim 12, where said spectral analysis, and/or external gas composition data is used to calculate the gas compressibility to adjust the gas mass flow calculation in real time.

15. Apparatus according to claim 1, comprising a signal control module for controlling a signal transmitted between said transducers for use in determination of said ultrasonic transit time, said signal control module being configured to, alternately or selectively cause one of: (i) a chirp signal, and (ii) an ultrasonic signal comprising a sequence of individual single frequency packets to be transmitted between said transducers.

16. Apparatus according to claim 1, wherein each transducer comprises a nozzle and wherein a pipe extends between the upstream transducer nozzle and the downstream transducer nozzle, and optionally wherein a pressure transmitter is provided in said pipe extending between said upstream and downstream transducers, and a flow parameter in the form of a pressure differential is measured between said upstream transducer nozzle and/or said downstream transducer nozzle and said pressure transmitter.

17. Apparatus according to claim 1, wherein each transducer comprises a nozzle and wherein a pipe extends between the upstream transducer nozzle and the downstream transducer nozzle, and optionally further including a dedicated chamber within said pipe and a non-invasive densitometer comprising an ultrasonic crystal or time-of-flight measuring device associated with said chamber for measuring the density of said gas flowing through said conduit.

18. Apparatus according to claim 1, wherein at least one of said transducers includes one or more additional pipe or spool nozzles.

19. A method of flare flow metering to obtain flow measurements in respect of flare gas in a flare line, comprising:
using an ultrasonic mass flow meter including a first, upstream ultrasonic transducer and a second, downstream transducer, each transducer being mounted in a peripheral wall of a conduit defining said flare line, at an angle to the flow of flare gas therethrough, to obtain data representative of an ultrasonic transit time between said transducers and calculating, using said data, a first flow velocity of said gas; using at least one measurement device to measure a flow parameter of said flow of gas through said conduit, calculating, using data representative of said flow parameter, a second flow velocity of said gas, selecting a preferred flow velocity from said first and second calculated flow velocities dependent upon expected accuracy in current gas flow conditions, and calculating, using said selected preferred flow velocity, a mass flow in respect of said gas flow.

20. A method of flow metering to obtain flow measurements in respect of a fluid in a conduit, comprising:
providing an ultrasonic mass flow meter including a first, upstream transducer and a second, downstream transducer mounted in a peripheral wall of said conduit at an angle to the flow of fluid therethrough;
transmitting from said first transducer to said second transducer an ultrasonic signal comprising a sequence of individual single frequency packets;
analysing each of the frequency packets received at said second transducer to identify any absorption of said signal by said fluid; and
using said frequency packets received at said second transducer to calculate a flow velocity of said fluid.

* * * * *